(12) United States Patent
Mansouri et al.

(10) Patent No.: US 6,589,591 B1
(45) Date of Patent: Jul. 8, 2003

(54) METHOD FOR TREATING MEDICAL DEVICES USING GLYCEROL AND AN ANTIMICROBIAL AGENT

(75) Inventors: Mohammad David Mansouri, Houston, TX (US); Rabih O. Darouiche, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/902,127

(22) Filed: Jul. 10, 2001

(51) Int. Cl.[7] .......................... A61L 27/00; A61L 28/00; B05D 1/00
(52) U.S. Cl. ...................... 427/2.24; 427/2.28; 427/2.3; 427/2.31; 427/2.25; 427/336; 427/348; 427/372.2; 427/430.1
(58) Field of Search ............................... 427/2.24, 2.25, 427/2.28, 2.3, 2.31, 336, 348, 372.2, 430.1

(56) References Cited

U.S. PATENT DOCUMENTS

| | | | |
|---|---|---|---|
| 3,954,467 A | * 5/1976 | Takimoto et al. ............ 430/87 |
| 4,107,121 A | 8/1978 | Stoy |
| 4,207,313 A | * 6/1980 | Umezawa et al. ............ 435/78 |
| 4,341,768 A | 7/1982 | Konishi et al. |
| 4,423,153 A | * 12/1983 | Ranney et al. ................. 435/6 |
| 4,442,133 A | 4/1984 | Greco et al. |
| 4,769,013 A | 9/1988 | Lorenz et al. |
| 4,895,566 A | 1/1990 | Lee |
| 4,917,686 A | 4/1990 | Bayston et al. |
| 4,952,419 A | 8/1990 | De Leon et al. |
| 5,013,306 A | 5/1991 | Solomon et al. |
| 5,197,977 A | 3/1993 | Hoffman, Jr. et al. |
| 5,217,493 A | 6/1993 | Raad et al. |
| 5,369,155 A | * 11/1994 | Asmus ........................ 523/111 |
| 5,498,416 A | * 3/1996 | Carsenti-Etesse et al. .. 424/422 |
| 5,507,777 A | * 4/1996 | Kus et al. .................... 264/145 |
| 5,624,704 A | * 4/1997 | Darouiche et al. ......... 427/2.24 |
| 5,628,785 A | 5/1997 | Schwartz et al. |
| 5,705,092 A | 1/1998 | Wellinghoff et al. |
| 5,756,145 A | 5/1998 | Darouiche |
| 5,830,539 A | 11/1998 | Yan et al. |
| 5,853,745 A | 12/1998 | Darouiche |
| 5,902,283 A | 5/1999 | Darouiche et al. |
| 5,939,208 A | 8/1999 | Stoy |
| 6,008,195 A | 12/1999 | Selsted |
| 6,054,504 A | 4/2000 | Dalla Riva Toma |
| 6,096,369 A | 8/2000 | Anders et al. |
| 6,162,487 A | 12/2000 | Darouiche |
| 6,166,007 A | 12/2000 | Sodemann |
| 6,172,163 B1 | * 1/2001 | Rein et al. ................... 264/136 |
| 6,322,847 B1 | * 11/2001 | Zhong et al. .............. 427/2.28 |
| 6,444,234 B1 | * 9/2002 | Kirby et al. ................. 424/725 |

* cited by examiner

Primary Examiner—Shrive P. Beck
Assistant Examiner—Jennifer Kolb Michener
(74) Attorney, Agent, or Firm—Fulbright & Jaworski, LLP

(57) ABSTRACT

A non-metallic medical device treated with a antimicrobial agents is provided. Different combinations of antimicrobial agents can be used for different types of non-metallic medical devices depending on the types of infections related to each device. The combination of different antimicrobial substances has a synergistic effect against certain bacteria and fungi. An antimicrobial agent can be used to treat a non-metallic medical device by mixing the antimicrobial agent with an acid solution and glycerol and exposing the non-metallic medical device to the resulting mixture such that an enough of the antimicrobial agent binds to a portion of the non-metallic medical device to inhibit the growth of bacterial and fungal organisms.

23 Claims, No Drawings

METHOD FOR TREATING MEDICAL DEVICES USING GLYCEROL AND AN ANTIMICROBIAL AGENT

FIELD OF INVENTIONS

The present invention relates to indwelling or implanted medical devices treated with an antimicrobial agent to inhibit the growth of bacterial and fungal organisms. The invention also relates to a method of treating indwelling or implanted medical devices with an antimicrobial agent.

BACKGROUND

Indwelling medical devices such as catheters are becoming essential to patient care. The benefit derived from these catheters, orthopedic devices, and other types of medical implants, however, is often offset by infectious complications.

Some of the common organisms causing infectious complications associated with indwelling medical devices are *Staphylococcus epidermidis* and *Staphylococcus aureus*. In the case of vascular catheters, these two organisms account for almost 70–80% of all infectious organisms, with *Staphylococcus epidermidis* being the most common organism. Gram-negative bacilli cause about 15–20% of the infections, and Candida species, a fungal agent, accounts for about 10–15% of the vascular catheter infections. Other gram-negative bacteria and fungal organisms (Candida) account for the remaining one-third of cases.

Another common hospital-acquired infection is a urinary tract infection (UTI). The majority of UTI cases are associated with the use of urinary catheters, including transurethral foley, suprapubic and nephrostomy catheters. These urinary catheters are inserted in a variety of populations, including the elderly, stroke victims, spinal cord-injured patients, postoperative patients and those with obstructive uropathy. Despite adherence to sterile guidelines for the insertion and maintenance of urinary catheters, catheter-associated UTI continues to pose a major problem. In the U.S. alone, about 1 million cases of hospital-acquired cases of UTI occur annually. For instance, it is estimated that almost one-quarter of hospitalized spinal cord-injured patients develop symptomatic UTI during their hospital course. Gram-negative bacilli account for almost 60–70%, enterococci for about 25% and Canada species for about 10% of cases of UTI.

Colonization of bacteria on the surfaces of the implant or other parts of the device can produce serious patient problems, including the need to remove and/or replace the implanted device and to vigorously treat secondary infective conditions. A considerable amount of attention and study has been directed toward preventing such colonization by the use of antimicrobial agents, such as antibiotics, bound to the surface of the materials employed in such devices. In such attempts, the objective has been to produce a sufficient bacteriostatic or bactericidal action to prevent colonization.

Various methods have previously been employed to prevent infection of medical devices. A simple method is to flush the surfaces of a device with an antimicrobial solution. Generally, this flushing technique requires convenient access to the implantable device. For example, catheters are generally amenable to flushing with a solution of rifampin and minocycline or rifampin and novobiocin. For use in flushing solutions, the effective concentration of the antibiotic range from about 1 to 10 mg/ml for minocycline, preferably about 2 mg/ml; 1 to 10 mg/ml for rifampin, preferably about 2 mg/ml; and 1 to 10 mg/ml for novobiocin, preferably about 2 mg/ml. The flushing solution is normally composed of sterile water or sterile saline solutions.

Other methods of coating surfaces of medical devices with antimicrobial agents are taught in U.S. Pat. No. 4,895,566 (a medical device substrate carrying a negatively charged group having a pKa of less than 6 and a cationic antibiotic bound to the negatively charged group); U.S. Pat. No. 4,917686 (antibiotics are dissolved in a swelling agent which is absorbed into the matrix of the surface material of the medical device); U.S. Pat. No. 4,107,121 (constructing the medical device with ionogenic hydrogels, which thereafter absorb or ironically bind antibiotics); U.S. Pat. No. 5,013,306 (laminating an antibiotic to a polymeric surface layer of a medical device); U.S. Pat. No. 4,95,419 (applying a film of silicone oil to the surface of an implant and then contacting the silicone film bearing surface with antibiotic powders); and U.S. Pat. No. 4,442,133.

These and other methods of coating medical devices with antimicrobial agents appear in numerous patents and medical journal articles. However, these methods also have significant drawbacks in that they can alter the integrity of non-metallic medical devices or result in residual antimicrobial material precipitating within the device.

Accordingly, there is a need for a non-metallic medical device treated with an antimicrobial agent to provide a broad range of antimicrobial activity while minimizing the harmful side effects noted above. Further, there is a need for a method that results in low residual coating material left on the surface of the medical device, which reduces complications arising from precipitation of coating material within the device. There is also a need to enhance the versatility of the treatment to accommodate higher concentrations of antimicrobial agents if needed.

SUMMARY OF THE INVENTION

One aspect of the present invention is a method for treating non-metallic medical devices with an antimicrobial agent comprising the steps of mixing at least an antimicrobial agent, an acid solution, and glycerol to form an antimicrobial composition and applying the antimicrobial composition to at least a portion of the non-metallic medical device under conditions wherein an effective concentration of the antimicrobial composition binds to the non-metallic medical device.

In a specific embodiment, the antimicrobial composition may be formed by mixing antimicrobial agents and an acid solution and then adding glycerol.

In another specific embodiment, the antimicrobial agent may be selected from the chlorhexidine and methylisothiazolone; chlorhexidine and α-terpineol; thymol and chloroxylenol; thymol and methylisothiazolone; chlorhexidine and cetylpyridinium chloride; chlorhexidine and chloroxylenol; chlorhexidine, methylisothiazolone and thymol; methylisothiazolone and α-terpineol; minocycline and rifampin; and chlorhexidine, methylisothiazolone and α-terpineol.

In another specific embodiment, the portion of the non-metallic medical device treated may be made from rubber, plastic, nylon, silicone, polyurethane, polyethylene, polyvinyl chloride, polytetrafluoroethylene tetraphthalate, polyethylene tetraphthalate, polytetrafluoroethylene, latex, elastomers, polymers, and materials sealed with gelatin, collagen or alumin.

In another specific embodiment, the non-metallic medical device may be a peripherally insertable central venous catheter, dialysis catheter, long term tunneled central venous catheter, peripheral venous catheter, short-term central venous catheter, arterial catheter, pulmonary artery Swan-Ganz catheter, urinary catheter, long term non-tunneled central venous catheters, peritoneal catheters, ventricular catheters, long term urinary devices, tissue bonding urinary devices, penile prostheses, vascular grafts, extravascular grafts, urinary stints, vascular catheter ports, wound drain tubes, hydrocephalus shunts, pacemaker systems, artificial urinary sphincters, vascular dialators, extravascular dialators, vascular stints, extravascular stints, small joint replacements, temporary joint replacements, urinary dilators, heart valves, orthopedic implants, heart assist devices, stents, penial implants mammary implants, and dental devices.

In another specific embodiment, the acid solution may be a short chain monocarboxylic acid and ortho-phosphoric acid. The short chain monocarboxylic acid may be formic acid, acetic acid, or propionic acid.

A further specific embodiment includes the ratio of monocarboxylic acid to ortho-phosphoric acid to glycerol may be about 79:8:13.

In another specific embodiment, the antimicrobial composition has a temperature that is between 2° C. to 75° C. at some point during the treatment, preferably about 45° C.

In another specific embodiment, the acid solution may also contain potassium chloride.

In another specific embodiment, the antimicrobial composition may be applied by exposing the non-metallic medical device to the antimicrobial composition for about 10 minutes to about 18 hours, preferably about 60 minutes.

In another specific embodiment, the method of treating the non-metallic miedical-device may further comprise the step of removing excess antimicrobial composition from the non-metallic medical device after the application step and then drying the non-metallic medical device. The non-metallic medical device may be dried for about 16 hour In another specific embodiment, the non-metallic medical device may be flushed with water after the drying step and may then be dried again for about 10 hours to about 24 hours.

A further embodiment of the invention provides for an implantable medical device comprising a body; one or more non-metallic surfaces on said body, glycerol, and an antimicrobial agent, wherein the glycerol and an effective concentration of the antimicrobial agent coat the one or more non-metallic surfaces.

In another specific embodiment, the antimicrobial agent may be selected from the group consisting of chlorhexidine and methylisothiazolone; chlorhexidine and α-terpineol; thymol and chloroxylenol; thymol and methylisothiazolone; chlorhexidine and cetylpyridinium chloride; chlorhexidine and chloroxylenol; chlorhexidine, methylisothiazolone and thymol; methylisothiazolone and α-terpineol; minocycline and rifampin; and chlorhexidine, methylisothiazolone and α-terpineol.

In another specific embodiment, the device may consist, at least in part, of rubber, plastic, silicone, polyurethane, polyethylene, polytetrafluoroethylene and polyethylene tetraphthalate and polyethylene tetraphthalate sealed with gelatin, collagen or albumin.

In another specific embodiment, the non-metallic medical device may be a peripherally insertable central venous catheter, dialysis catheter, long term tunneled central venous catheter, peripheral venous catheter, short-term central venous catheter, arterial catheter, pulmonary artery Swan-Ganz catheter, urinary catheter, long term non-tunneled central venous catheters, peritoneal catheters, ventricular catheters, long term urinary devices, tissue bonding urinary devices, penile prostheses, vascular grafts, extravascular grafts, urinary stints, vascular catheter ports, wound drain tubes, hydrocephalus shunts, pacemaker systems, artificial urinary sphincters, vascular dialators, extravascular dialators, vascular stints, extravascular stints, small joint replacements, temporary joint replacements, urinary dilators, heart valves, orthopedic implants, heart assist devices, stents, penial implants, mammary implants, and dental devices.

DETAILED DESCRIPTION

It is readily apparent to one skilled in the art that various embodiments and modifications may be made to the invention disclosed in this application without departing from the scope and spirit of the invention.

As used in the specification, "a" or "an" means one or more. As used in the claims (s), when used in conjunction with the word "comprising," the words "a" or "an" mean more or more. As used herein, "another" means at least a second or more.

The term "antimicrobial agent" as used in the present invention means any single or combination of antiseptics, antibiotics, disinfectants, and antimicrobial peptides. Some examples antimicrobial agents include, but are not limited to, methylisothiazolone, thymol, α-terpineol, cetylpyridinium chloride, chloroxylenol, hexachlorophene, chlorhekidine and other cationic biguanides, methylene chloride, iodine and iodophores, triclosan, taurinamides, nitrofurantoin, methenamine, aldehydes, azylic acid, silver, benzyl peroxide, alcohols, carboxylic acids, salts, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicilins, cephlalosporins, carbepenems, beta-lactams antibiotics, aminoglycosides, macrolides, lincosamides glycopeeptides, tetracylines, chloramphenicol, quinolones, fucidines, sulfonamides, trimethoprims, rifamycins, oxalines, streptogramins, lipepeptides, ketolides, polyenes, azoles, and echinocandines. Other examples of antibiotics, such as those listed in Sakamoto et al, U.S. Pat. No. 4,642,104 herein incorporated by reference will readily suggest themselves to those of ordinary skill in the art.

These antimicrobial agents preferably used in combinations of two or more to obtain a synergistic effect. They are dispersed along the surface of the medical device to provide a broad range of antimicrobial activity.

Some examples include chlorhexidine and methylisothiazolone; chlorhexidine and α-terpineol; thymol and chloroxylenol; thymol and methylisothiazolone; chlorhexidine and cetylpyridinium chloride; chlorhexidine and chloroxylenol; chlorhexidine, methylisothiazolone and thymol; methylisothiazolone and α-terpineol; minocycline and rifampin; and chlorhexidine, methylisothiazolone and α-terpineol. These combinations provide a broad spectrum of activity against a wide variety of organisms.

The amount of antimicrobial agent used to treat a medical device varies to some extent, but is at least a sufficient amount to form an effective concentration to inhibit the growth of bacterial and fungal organisms, such as staphylococci, gram-positive bacteria, gram-negative bacilli and Candida.

The term "effective concentration" means a sufficient amount of an antimicrobial agent to decrease, prevent or inhibit the growth of bacterial and/or fungal organisms. The amount will vary for each compound and upon known factors such as pharmaceutical characteristics; the type of medical device; age, sex, health and weight of the recipient, and the use and length of use. It is within the skilled artisan's ability to relatively easily determine an effective concentration of an antimicrobial agent for different antimicrobial agents and different known factors.

The antimicrobial agents may antiseptics. The use of antiseptics may provide more efficacy against gram-negative bacteria and Candida species than antibiotic combinations. Although the different mixtures of antiseptics can be used for all medical devices, certain mixtures work better with different devices. Different combinations of antiseptics can be used for different types of medical devices depending on the spectrum of organisms that cause the infections related to each device. For instance, preferred combinations of treating orthopedic devices include chlorhexidine, methylisothiazolone and α-terpineol; chlorhexidine and cetylpyridinium chloride; chlorhexidine and chloroxylenol; or chlorhexidine, methylisothiazolone and thymol. The combination of different antiseptics has a synergistic effect against certain bacteria and fungi.

The term "bacterial and fungal organisms" as used in the present invention means all genera and species of bacteria and fungi, including but not limited to all spherical, rod-shaped and spiral organisms. One skilled inthe art recognizes that a variety of source books which list and describe bacteria and fungi are available, for example in the textbook "Principles and Practice of Infectious Diseises", Mandell et al., 4$^{th}$ edition, 1995, Churchill Livingstone, N.Y. Some examples of bacteria are staphylococci (i.e. *Staphylococcus epidermidis, Staphylococcus aureus*), Enterococcus faecalis, Pseudomonas aeruginosa, *Escherichia coli*, other gram-positve bactera and gram-negative bacilli. One example of a fungus is *Candida albicans:*

The term "glycerol" means glycerol or glyceride.

As used herein "implanted" devices includes both temporary and permanent devices and indwelling and implanted devices.

The medical devices which are amenable to treatment according to one aspect of the present invention are non-metallic. However, non-metallic portions or components of metallic devices may be treated. Treatable medical devices may also include devices that are formed from more than one type of non-metallic material.

Non-metallic materials that can be treated by the method of the present invention include, but are not limited to, rubber, plastic, nylon, silicone, polyurethane, polyethylene, polyvinyl chloride, Gortex (polytetrafluoroethylene tetraphthalate), Dacron (polyethylene tetraphthalate), Teflon (polytetrafluoroethylene), latex, elastomers, polymers, and materials sealed with gelatin, collagen or albumin.

Particular non-metallic medical devices suited for the antimicrobial treatment of the present invention include, but are not limited to, peripherally insertable central venous catheters, dialysis catheters, long term tunneled central venous catheters, long term non-tunneled central venous catheters, peripheral venous catheters, short-term central venous catheters, arterial catheters, pulmonary arty Swan-Ganz catheters, urinary catheters, long term urinary devices, tissue bonding urinary devices, penile prostheses, vascular grafts, extravascular grafts, urinary stints, vascular catheter ports, wound drain tubes, hydrocephalus shunts, peritoneal catheters, pacemaker systems, artificial urinary sphincters, vascular dialators, extravascular dialators, vascular stints, extravascular stints, ventricular catheters, small joint replacements, temporary -joint replacements, urinary dilators, heart valves, orthopedic implants, heart assist devices, stents, penial implants, mammary implants, dental devices, and the like.

In addition to treating non-metallic medical devices, the present invention may also be used to treat miscellaneous surfaces, such as hospital floors, nursing counters, counters adjacent to washing basins, desks, etc. to decrease transmission of hospital antibiotic-resistant microbial flora, such as methicillin-resistant *staphylococcus aureus*, vancomycin-resistant enterococci and antibiotic-resistant gram negative bacteria on the skin of health care personnel and patients. Another potential application is the treatment of kitchen counters to decrease transmission of organisms that cause food-borne poisoning, such as Salmonella species and *Escherichia coli.*

The non-metallic medical device may be treated with an antimicrobial composition by applying a sufficient amount of the antimicrobial composition to at least a portion of the medical device under conditions wherein at least a portion of the antimicrobial composition binds with the non-metallic portions of the medical device. Although it is contemplated that the antimicrobial agents will bind with the medical device, other ingredients such as anti coagulants and anti-inflammatory agents may be included in the antimicrobial composition and may also bind with the medical device. It is also contemplated that a non-metallic medical device may be treated with a composition of non-antimicrobial agents.

The following examples are offered by way of illustration and are not intended to limit the invention in any manner.

EXAMPLE 1

Method for Treating Non-Metallic Medical Devices

The treatment solution consists of a solvent of a saturated short chain monocarboxylic acid such as formic acid, acetic acid, and propionic acid with a liquidity state below 90° C. and above 10° C. and a pKa of 3 to 5. The formic acid solution is 88% formic acid. It is mixed with an 85% ortho-phosphoric acid solution (for uniformity of coating), 10 mg of potassium chloride per ml of the mixture of formic acid and ortho-phosphoric acid to get a homogeneous solution (potassium ions facilitate surface binding by increasing the ionic strength), and glycerol. The glycerol or glycerin is used as a plasticizer and a vehicle solvent. It also acts as a lubricant between polymer chains to prevent the polymer from becoming brittle during the treatment process. The glycerol also forms hydrogen bonding with its hydroxyl groups [—OH] with the polymer as well as the antimicrobial agents during the treatment process facilitating the incorporation of coating agents (antimicrobial or non-antimicrobial) into the medical device. The total volume of the resulting coating mixture can be composed of 79% formic acid solution (range between 10% to 90%), 8% ortho-phosphoric acid solution (range between 5% to 10%), and 13% glycerin (range between 8% to 15%). The antimicrobial agents (such as minocycline and rifampin) are added to the solution before addition of glycerin to avoid dissolution at a higher viscosity that glycerin adds to the coating solution. For instance, minocycline and rifampin are added at concentrations of up to 300 mg per ml of the total volume of the coating solution. The addition order of these antibiotics is not important; however, monitoring the dissolution of minocycline is easier before adding rifampin. Before immersing the non-metallic medical devices in the final treating solution, the solution's temperature should be elevated from the room temperature to around 45° C. (range between 2° C. to 75° C.) but well below the lowest boiling point of any component. At lower temperatures the treatment time may be increased up to 18 hours. After reaching the desired temperature, the device is completely submerged into the solution for a period of time that can vary depending on the nature of the polymer to be coated. This period can be 1 hour with a range between about 10 minutes to about 18 hours. However, for more rigid polymers such as polyethylene or polytetrafluoroethylene this period also could be elongated accordingly as long as the integrity of the polymer remains intact. The coating and drying steps should be preformed primarily in the dark to avoid unwanted free radical reactions.

After the treatment period, the device is removed and shaken vigorously or purged with nitrogen gas to remove any excess solution from the device. The device is then placed under a well-ventilated fume hood for at least 16 hours (it is recommended to dry for 48 hours to insure removal of excess glycerin and formic acid). This drying step is optimally performed in the dark. After the drying period the device is rinsed and flushed with deionized water and placed back under the fume hood for another 10–24 hour period.

EXAMPLE 2

Synergy of an Antiseptic Combination Used to Treat Non-Metallic Medical Devices

Catheter segments were coated with a solution containing 30 ml of 88% formic acid, 3 ml of 85% ortho-phosphoric acid, 400 mg of potassium chloride, 2000 mg of rifamnpin (50 mg/ml), 1000 mg of minocycline (25 mg/ml), and 5 ml of glycerol at a total of about 40 ml final solution according to the described method for one hour at 45° C. After the rinsing and drying process the antimicrobial activity of the coated catheters were measured by performing a modified Kirby-Bauer method. Three one-centimeter segments were set aside for each organism for baseline antimicrobial activity. Another twelve segments were placed in serum at 37° C. for each organism tested. Samples were removed after 3 days, 7 days, 10 days, and 14 days. After removal of samples from serum, the remaining segments were placed in new serum. Zones of inhibition were performed for baseline, day 3, day 7, day 10, and day 14 against *Staphylococcus epidermidis*, *Escherichia coli*, and *Candida albicans* according to Kirby-Bauer method. Each segment was half embedded in the center of a Muller-Hinton agar plate that had been previously inoculated with individual organisms. Prior to placing the segments in agar, each organism was grown for 18 hours in trypticase soy broth to a concentration of 0.5 McFarland U ($10^8$ cfu/ml). A cotton swab was placed in the suspension and streaked across the surface of the Muller-Hinton agar plate to cover the entire plate. All plates were placed in a 37° C. incubator for 24 hours.

Zones of inhibition were measured the next day. The results are shown in Table 1. Additionally, medical devices with different outside diameters were treated in the same way. The measured zones of inhibition for these medical devices are shown in Table 2. Tables 1 and 2 demonstrate the broad-spectrum antimicrobial activity that can be achieved using the disclosed treatment method.

TABLE 1

Mean Zones of Inhibition with Minocycline/Rifampin Coated Nylon Catheters (External Diameter, 1 mm)

|  | Staphylococcus Epidermidis | Escherichia coli | Candida albicans |
|---|---|---|---|
| Baseline (day 0) | 40 | 10 | 8 |
| Day 3 | 31 | 5 | Not done |
| Day 7 | 32 | 3 | Not done |
| Day 10 | 22 | 3 | 3 |
| Day 15 | 21 | — | — |

TABLE 2

Mean Zones of Inhibition with other Minocycline/Rifampin Coated Catheters (mm)

| Catheter (external diameter) | Staphylococcus epidermidis | Escherichia coli |
|---|---|---|
| Polyurethane introducer (4 mm) | 37 | 13 |
| Polyurethane catheter (2 mm) | 40 | 12 |
| Silicone catheter (1 mm) | 32 | 10 |

EXAMPLE 3

Non-Metallic Medical Devices Treated with an Antiseptic Composition or an Antibiotic Composition Using Two Different Acid Solutions Vascular catheters made out of four different materials were tested. The catheters were made out of nylon, polyurethane, silicone, and polyethylene. 6-cm catheter sections were treated using either Butyl acetate/Methanol (85:15) (BA/ME) or Formic acid/Potassium chloride/Phosphoric acid/Glycerin (30 ml:400 mg:3 ml:5 ml (FA/GL). The chloroxylenol was dissolved in formic acid at 45° C. for 2 hours with low agitation. The treatment solution used in the BA/ME method contained either 25 mg/ml of minocycline and 40 mg/ml of rifampin, or 50 mg/ml of chlorhexidine and 50 mg/ml of chloroxylenol. The treatment solution used in the FA/GL method contained either 25 mg/ml of minocycline and 50 mg/ml of rifampin, or 100 mg/ml of chlorhexidine and 100 mg/ml of chloroxylenol.

The catheter sections were immersed in the treatment solution for 60 minutes in the dark. The Catheter sections were then removed from the treatment solutions and dried for 24 hours under a fume hood in the dark. Finally, the catheter sections were rinsed with deionized distilled water and placed back under the fume hood for another 24 hours in the dark.

After the catheter sections were allowed to dry, 0.5-cm pieces were cut from the end of each catheter section and disposed, and the remaining 5-cm coated catheter sections were cut into five 1-cm segments. The 1-cm coated catheter segments were used to determine the zone of inhibition (measurement that represents the diameter of the clear zone perpendicular to the long axis of the 1–2 mm wide catheter segment) against 3 types of organisms (*Staphylococcus epidermidis*, *Escherichia coli*, and *Candida albicans*), both at baseline (day 0) and after incubation in serum at 37° C. (day 1, day 3, day 7, and day 14). The serum was replaced with new serum at days 1, 3, and 7. The zones of inhibition were determined in triplicate for each of the specific groups (stratified according to type of coating method/type of antimicrobial coating agents/type of catheter material/type of organism/time of performing zone of inhibition.)

The results are shown in Tables 3–6. The tables further demonstrate the broad-spectrum antimicrobial activity achieved using the disclosed treatment method. Tables 3–6 further demonstrate that the disclosed method can be used to effectively treat various types of non-metallic materials.

TABLE 3

BA/ME Coating Method Using Minocycline/Rifampin (25M/40R) Average Zones of Inhibition in mm (Average of 3 Observations)

| Duration | Organism | Polyurethane | Nylon | Silicone | Polyethylene |
| --- | --- | --- | --- | --- | --- |
| Baseline | Staph. epi. | 33 | 17 | 31 | 18 |
| 1 Day | Staph. epi. | 31 | 16 | 31 | 16 |
| 3 Days | Staph. epi. | 31 | 14 | 29 | 17 |
| 7 Days | Staph. epi. | 29 | 7 | 22 | 10 |
| 14 Days | Staph. epi. | 27 | 5 | 14 | 0 |
| Baseline | E. coli | 8 | 2 | 8 | 0 |
| 1 Day | E. coli | 5 | 0 | 10 | 0 |
| 3 Days | E. coli | 4 | 0 | 0 | 0 |
| 7 Days | E. coli | 4 | 0 | 0 | 0 |
| 14 Days | E. coli | 5 | 0 | 0 | 0 |
| Baseline | Candida a. | 12 | 0 | 13 | 0 |
| 1 Day | Candida a. | 9 | 0 | 6 | 0 |
| 3 Days | Candida a. | 7 | 0 | 3 | 0 |
| 7 Days | Candida a. | 5 | 0 | 0 | 0 |
| 14 Days | Candida a. | 0 | 0 | 0 | 0 |

TABLE 4

BA/ME Coating Method Using Chlorhexidine/Chloroxylenol (50CH/50CX) Average Zones of Inhibition in mm (Average of 3 Observations)

| Duration | Organism | Polyurethane | Nylon | Silicone | Polyethylene |
| --- | --- | --- | --- | --- | --- |
| Baseline | Staph. epi. | 17 | 7 | 12 | 0 |
| 1 Day | Staph. epi. | 14 | 6 | 11 | 0 |
| 3 Days | Staph. epi. | 12 | 6 | 10 | 0 |
| 7 Days | Staph. epi. | 12 | 5 | 8 | 0 |
| 14 Days | Staph. epi. | 8 | 5 | 3 | 0 |
| Baseline | E. coli | 14 | 4 | 10 | 2 |
| 1 Day | E. coli | 9 | 2 | 7 | 0 |
| 3 Days | E. coli | 8 | 0 | 6 | 0 |
| 7 Days | E. coli | 7 | 0 | 3 | 0 |
| 14 Days | E. coli | 5 | 0 | 0 | 0 |
| Baseline | Candida a. | 19 | 3 | 13 | 0 |
| 1 Day | Candida a. | 11 | 2 | 13 | 0 |
| 3 Days | Candida a. | 10 | 0 | 4 | 0 |
| 7 Days | Candida a. | 9 | 0 | 0 | 0 |
| 14 Days | Candida a. | 2 | 0 | 0 | 0 |

TABLE 5

FA/GL Coating Method Using Minocycline/Rifampin (25M/50R) Average Zones of Inhibition in mm (Average of 3 Observations)

| Duration | Organism | Polyurethane | Nylon | Silicone | Polyethylene |
| --- | --- | --- | --- | --- | --- |
| Baseline | Staph. epi. | 35 | 28 | 23 | 23 |
| 1 Day | Staph. epi. | 32 | 24 | 16 | 9 |
| 3 Days | Staph. epi. | 27 | 17 | 18 | 6 |
| 7 Days | Staph. epi. | 23 | 15 | 10 | 3 |
| 14 Days | Staph. epi. | 23 | 11 | 4 | 2 |
| Baseline | E. coli | 7 | 12 | 6 | 10 |
| 1 Day | E. coli | 4 | 4 | 6 | 4 |
| 3 Days | E. coli | 0 | 3 | 7 | 2 |
| 7 Days | E. coli | 0 | 3 | 6 | 0 |

TABLE 5-continued

FA/GL Coating Method Using Minocycline/Rifampin (25M/50R) Average Zones of Inhibition in mm (Average of 3 Observations)

| Duration | Organism | Polyurethane | Nylon | Silicone | Polyethylene |
| --- | --- | --- | --- | --- | --- |
| 14 Days | E. coli | 0 | 0 | 2 | 0 |
| Baseline | Candida a. | 6 | 5 | 5 | 3 |
| 1 Day | Candida a. | 6 | 4 | 2 | 0 |
| 3 Days | Candida a. | 4 | 2 | 0 | 0 |
| 7 Days | Candida a. | 4 | 0 | 0 | 0 |
| 14 Days | Candida a. | 4 | 0 | 0 | 0 |

TABLE 6

FA/GL Coating Method Using Chlorhexidine/Chloroxylenol (100CH/100CX) Average Zones of Inhibition in mm (Average of 3 Observations)

| Duration | Organism | Polyurethane | Nylon | Silicone | Polyethylene |
| --- | --- | --- | --- | --- | --- |
| Baseline | Staph. epi. | 33 | 33 | 20 | 18 |
| 1 Day | Staph. epi. | 30 | 31 | 17 | 12 |
| 3 Days | Staph. epi. | 30 | 26 | 14 | 10 |
| 7 Days | Staph. epi. | 28 | 23 | 12 | 21 |
| 14 Days | Staph. epi. | 26 | 27 | 14 | 10 |
| Baseline | E. coli | 19 | 21 | 21 | 15 |
| 1 Day | E. coli | 20 | 18 | 11 | 8 |
| 3 Days | E. coli | 20 | 18 | 9 | 6 |
| 7 Days | E. coli | 18 | 16 | 8 | 6 |
| 14 Days | E. coli | 21 | 17 | 7 | 7 |
| Baseline | Candida a. | 40 | 37 | 40 | 16 |
| 1 Day | Candida a. | 39 | 32 | 22 | 4 |
| 3 Days | Candida a. | 32 | 28 | 19 | 6 |
| 7 Days | Candida a. | 25 | 23 | 15 | 2 |
| 14 Days | Candida a. | 32 | 25 | 7 | 3 |

All patents and publication mentioned in this specification are indicative of the levels of those skilled in the art to which the invention pertains. All patents and publications. are herein incorporated by reference to the same extent as if each individual publication was specifically and individually indicated to be incorporated by reference.

The present invention, therefore, is well adapted to carry out the objects and attain the ends and advantages mentioned as well as other inherent therein. While presently preferred embodiments of the invention are given for the purpose of disclosure, numerous changes in the details will readily suggest themselves to those skilled in the art and which are encompassed within the spirit of the invention; and the scope of the appended claims.

What is claimed is:

1. A method of treating a non-metallic medical device with an antimicrobial agent comprising the steps of:
   mixing at least an antimicrobial agent, an acid solution, wherein said acid solution is comprised of short chain monocarboxylic acid and ortho-phosphoric acid, and glycerol to form an antimicrobial composition; and
   applying the antimicrobial composition to at least a portion of the non-metallic medical device under conditions wherein an effective concentration of the antimicrobial composition binds to the non-metallic medical device.

2. The method of claim 1, wherein the antimicrobial composition is formed by mixing the antimicrobial agents and the acid solution and then adding glycerol.

3. The method according to claim 1, wherein the antimicrobial agent is selected from the group of combinations consisting of chlorhexidine and methylisothiazolone; chlorhexidine and α-terpineol; thymol and chloroxylenol; thymol and methylisothiazolone; chlorhexidine and cetylpyridinium chloride; chlorhexidine and chloroxylenol; chlorhexidine, methylisothiazolone and thymol; methylisothiazolone and α-terpineol; minocycline and rifampin; and chlorhexidine, methylisothiazolone and α-terpineol.

4. The method according to claim 1, wherein the antimicrobial agent is comprised of a minocycline and rifampin.

5. The method according to claim 1, wherein a portion of the non-metalic medical device is made from material selected from the group consisting of rubber, plastic, nylon, silicone, polyurethane, polyethylene, polyvinyl chloride, polytetrafluoroethylene terephthalate, polyethylene terephthalate, polytetrafluoroethylene, latex, and materials sealed with gelatin, collagen or albumin.

6. The method according to claim 1, wherein the non-metallic medical device is a catheter selected from the group consisting of peripherally insertable central venous catheter, dialysis catheter, long term tunneled central venous catheter, peripheral venous catheter, short-term central venous catheter, arterial catheter, pulmonary artery Swan-Ganz catheter, urinary catheter, long term non-tunneled central venous catheters, peritoneal catheters, and ventricular catheters.

7. The method according to claim 1, wherein the non-metallic medical device is selected from the group consisting of long term urinary devices, t issue bonding urinary devices, penile prostheses, vascular grafts, extravascular grafts, urinary stints, vascular catheter ports, wound drain tubes, hydrocephalus shunts, pacemaker systems, artificial urinary sphincters, vascular dialators, extravascular dialators, vascular stints, extravascular stints, small joint replacements, temporary joint replacements, urinary dilators, heart valves, orthopedic implants, heart assist devices, stents, penial implants, mammary implants, and dental devices.

8. The method according to claim 1, wherein the volume ratio for monocarboxylic acid to ortho-phosphoric acid to glycerol is about 79:8:13.

9. The method according to claim 1, wherein the short chain monocarboxylic acid is selected from the group consisting of fouric acid, acetic acid, and propionic acid.

10. The method according to claim 1, wherein the antimicrobial composition has a temperature that reaches between 2° C. to 75° C. during the applying step.

11. The method according to claim 1, wherein the antimicrobial composition has a temperature that reaches about 45° C. during the applying step.

12. The method according to claim 1, wherein the acid solution further comprises potassium chloride.

13. The method according to claim 1, wherein the antimicrobial composition is applied by exposing the non-metallic medical device to the antimicrobial composition for about 10 minutes to about 18 hours.

14. The method according to claim 1, wherein the antimicrobial composition is applied by exposing the non-metallic medical device to the antimicrobial composition for about 60 minutes.

15. The method according to claim 1, further comprising the step of:
    removing excess antimicrobial composition from the non-metallic medical device after applying the antimicrobial composition; and drying the non-metallic medical device after removing the excess antimicrobial composition.

16. The method according to claim 15, wherein the excess antimicrobial composition is removed with gaseous material.

17. The method according to claim 16, wherein the gaseous material is nitrogen.

18. The method according to claim 15, wherein the drying step lasts for about 16 hours.

19. The method according to claim 15, further comprising the step of flushing the non-metallic medical device with water after the drying step.

20. The method according to claim 19, further comprising drying the non-metallic medical device after flushing the non-metallic medical device with water.

21. The method according to claim 19, further comprising drying the non-metallic medical device from about 10 hours to about 24 hours after flushing the non-metallic medical device with water.

22. The method according to claim 1, wherein the antimicrobial agent is applied by dipping the non-metallic medical device into the antimicrobial composition.

23. The method of claim 1, wherein the short chain monocarboxylic acid has a pKa of 3–5.

* * * * *